US00PP23781P2

(12) United States Plant Patent
Kraan

(10) Patent No.: US PP23,781 P2
(45) Date of Patent: Jul. 30, 2013

(54) ***WEIGELA* PLANT NAMED 'BOKRASPIWI'**

(50) Latin Name: *Weigela hybrida*
Varietal Denomination: Bokraspiwi

(75) Inventor: Kees Jan Kraan, Papenveer (NL)

(73) Assignee: Spring Meadow Nursery Inc., Grand Haven, MI (US)

( * ) Notice: Subject to any disclaimer, the term of this patent is extended or adjusted under 35 U.S.C. 154(b) by 89 days.

(21) Appl. No.: 13/200,530

(22) Filed: Sep. 23, 2011

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — C. A. Whealy

(57) ABSTRACT

A new and distinct cultivar of *Weigela* plant named 'Bokraspiwi', characterized by its compact, uniform and low mounding plant habit; freely branching habit; dark grayed purple-colored leaves; red purple-colored flowers; and good garden performance.

2 Drawing Sheets

Botanical designation: *Weigela hybrida.*
Cultivar denomination: 'BOKRASPIWI'.

BACKGROUND OF THE INVENTION

The present invention relates to a new and distinct cultivar of *Weigela* plant, botanically known as *Weigela hybrida* and hereinafter referred to by the name 'Bokraspiwi'.

The new *Weigela* plant is a product of a planned breeding program conducted by the Inventor in Boskoop, The Netherlands. The objective of the breeding program was to develop new compact *Weigela* plants with attractive leaf and flower colors.

The new *Weigela* plant originated from an open-pollination during the summer of 2000 of a proprietary selection of *Weigela hybrida* identified as code number 93115, not patented, as the female, or seed, parent with an unknown selection of *Weigela hybrida* as the male, or pollen, parent. The new *Weigela* plant was discovered and selected by the Inventor in June, 2007 as a single flowering plant from within the progeny of the stated open-pollination in a controlled environment in Boskoop, The Netherlands.

Asexual reproduction of the new *Weigela* plant by softwood cuttings in Boskoop, The Netherlands since the summer of 2007 has shown that the unique features of this new *Weigela* plant are stable and reproduced true to type in successive generations of asexual reproduction.

SUMMARY OF THE INVENTION

Plants of the new *Weigela* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Bokraspiwi'. These characteristics in combination distinguish 'Bokraspiwi' as a new and distinct *Weigela* plant:

1. Compact, uniform and low mounding plant habit.
2. Freely branching habit.

3. Dark grayed purple-colored leaves.
4. Red purple-colored flowers.
5. Good garden performance.

In side-by-side comparisons conducted in Boskoop, The Netherlands, plants of the new *Weigela* differ from plants of the female parent selection primarily in the following characteristics:

1. Plants of the new *Weigela* are more compact and denser than plants of the female parent selection.
2. Plants of the new *Weigela* have narrower and darker-colored leaves than plants of the female parent selection.
3. Plants of the new *Weigela* and the female parent selection differ in flower color.

Plants of the new *Weigela* can be compared to plants of the *Weigela florida* 'Bramwell', disclosed in U.S. Plant Pat. No. 18,513. In side-by-side comparisons in Boskoop, The Netherlands, plants of the new *Weigela* differed from plants of 'Bramwell' in the following characteristics:

1. Plants of the new *Weigela* were more outwardly spreading than plants of 'Bramwell'.
2. Plants of the new *Weigela* had darker colored leaves than plants of 'Bramwell'.
3. Plants of the new *Weigela* and 'Bramwell' differed in flower color as plants of 'Bramwell' had pink-colored flowers.

Plants of the new *Weigela* can be compared to plants of the *Weigela florida* 'Alexandra', disclosed in U.S. Plant Pat. No. 10,772. In side-by-side comparisons in Boskoop, The Netherlands, plants of the new *Weigela* differed from plants of 'Alexandra' in the following characteristics:

1. Plants of the new *Weigela* were more compact than plants of 'Alexandra'.
2. Plants of the new *Weigela* had darker colored leaves than plants of 'Alexandra'.
3. Plants of the new *Weigela* and 'Alexandra' differed in flower color as plants of 'Alexandra' had lighter-colored flowers.

BRIEF DESCRIPTION OF THE PHOTOGRAPHS

The accompanying colored photographs illustrate the overall appearance of the new *Weigela* plant showing the colors as true as it is reasonably possible to obtain in colored reproductions of this type. Colors in the photographs may differ slightly from the color values cited in the detailed botanical description which accurately describe the colors of the new *Weigela* plant.

The photograph on the first sheet comprises a side perspective view of a typical vegetative plant of 'Bokraspiwi' grown in a container.

The photograph on the second sheet is a close-up view of a typical flowering plant of 'Bokraspiwi'.

DETAILED BOTANICAL DESCRIPTION

The aforementioned photographs, following observations and measurements describe plants grown in gallon containers during the spring and early summer in an outdoor nursery in Grand Haven, Mich. and under commercial production practices. Plants were 3.5 years old when the photographs and description were taken. In the following description, color references are made to The Royal Horticultural Society Colour Chart, 2001 Edition, except where general terms of ordinary dictionary significance are used.

Botanical classification: *Weigela hybrida* 'Bokraspiwi'.

Parentage:

*Female or seed, parent*.—Proprietary selection of *Weigela hybrida* identified as code number 93115, not patented.

*Male or pollen, parent*.—Unknown selection of *Weigela hybrida*, not patented.

Propagation:

*Type*.—By softwood cuttings.

*Time to initiate roots*.—About 30 days at temperatures of 20° C.

*Time to produce a rooted young plant*.—About six months at temperatures of 18° C.

*Root description*.—Medium in thickness; light brown in color.

*Rooting habit*.—Moderately freely branching; medium in density.

Plant description:

*Plant and growth habit*.—Perennial shrub; compact, uniform and low mounding plant habit; vigorous growth habit.

*Branching habit*.—Freely branching habit with numerous lateral branches developing per plant; dense and bushy plant form.

*Plant height*.—About 30 cm.

*Plant diameter*.—About 60 cm.

Lateral branch description:

*Length*.—About 45 cm.

*Diameter*.—About 4 mm.

*Internode length*.—About 4.5 cm.

*Strength*.—Moderately strong to strong.

*Aspect*.—About 20° to 40° from vertical.

*Texture*.—Slightly pubescent.

*Color*.—Close to 202A.

Foliage description:

*Arrangement*.—Opposite; simple.

*Length*.—About 8 cm.

*Width*.—About 3.6 cm.

*Shape*.—Elliptic to oblanceolate.

*Apex*.—Acute to acuminate.

*Base*.—Cuneate to attenuate.

*Margin*.—Serrulate; undulating.

*Texture, upper and lower surfaces*.—Smooth, glabrous.

*Venation pattern*.—Pinnate.

*Color*.—Developing leaves, upper and lower surfaces: Close to 202A. Fully expanded leaves, upper and lower surfaces: Close to 187A; venation, close to 143C.

*Petiole*.—Length: About 6 mm. Diameter: About 2 mm. Texture, upper and lower surfaces: Smooth, glabrous. Color, upper and lower surfaces: Close to 143C.

Flower description:

*Flower arrangement and habit*.—Salverform flowers arranged in clusters of about twelve flowers; flowers face upright or outwardly to slightly drooping.

*Fragrance*.—None detected.

*Natural flowering season*.—Plants of the new *Weigela* flower from late May to early June in Grand Haven, Mich.

*Flower longevity*.—Flowers last about three to six weeks on the plant; flowers not persistent.

*Flower diameter*.—About 2.5 cm.

*Flower length* (*height*).—About 6 cm.

*Flower bud*.—Length: About 4 mm. Diameter: About 2 mm. Shape: Tubular to oblong. Color: Close to 202A.

*Corolla*.—Arrangement: Salverform; five petals fused into a long tube with separate petal lobes. Petal lobe length: About 1 cm. Petal lobe width: About 1.2 cm. Petal lobe shape: Elliptic to obovate. Petal lobe apex: Obtuse. Petal lobe margin: Entire. Petal texture, upper and lower surfaces: Smooth, glabrous. Color: When opening and fully opened, upper surface: Close to 60D. When opening and fully opened, lower surface: Close to between 59C and 58A.

*Sepals*.—Quantity per flower: Five in a single whorl, fused; campanulate calyx. Length: About 1 cm. Width: About 2 mm. Shape: Lanceolate. Apex: Narrowly acute. Margin: Entire. Sepal texture, upper and lower surfaces: Smooth; glabrous. Color, upper and lower surfaces: Close to 202A.

*Peduncles*.—Length: About 1 cm. Diameter: About 1 mm. Angle: About 10° to 20° from stem axis. Strength: Moderately strong; flexible. Texture: Smooth, glabrous. Color: Close to 202A.

*Reproductive organs*.—Stamens: Quantity/arrangement: Five per flower. Anther shape: Narrowly oblong. Anther size: About 1 mm by 3 mm. Anther color: Close to 160C. Pollen amount: Moderate. Pollen color: Close to 160C. Pistils: Quantity: One per flower. Pistil length: About 5.8 cm. Style length: About 3.6 cm. Style color: Close to 65B. Stigma color: Close to 160C. Ovary color: Close to 202A. Seeds and fruits: Seed and fruit development has not been observed on plants of the new *Weigela*.

Garden performance: Plants of the new *Weigela* have exhibited good tolerance to rain, wind and have been observed to tolerate temperatures from about −29° C. to about 33° C.

Pathogen/pest resistance: Plants of the new *Weigela* have not been observed to be resistant to pests and pathogens common to *Weigela*.

It is claimed:

1. A new and distinct *Weigela* plant named 'Bokraspiwi' as illustrated and described.

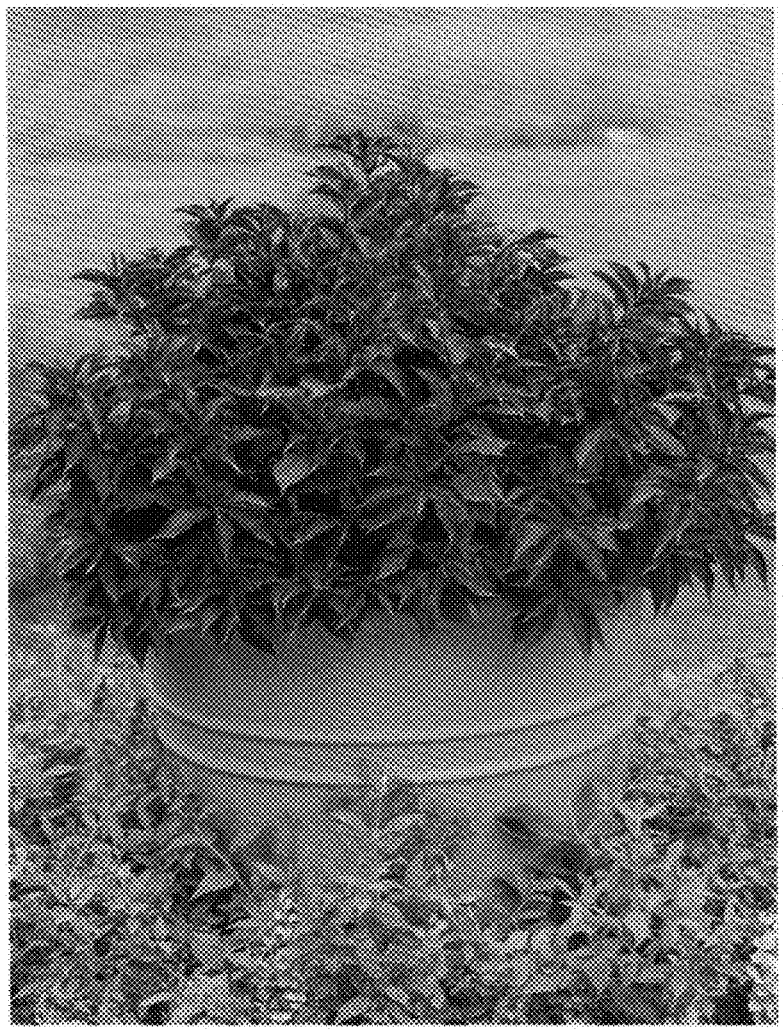

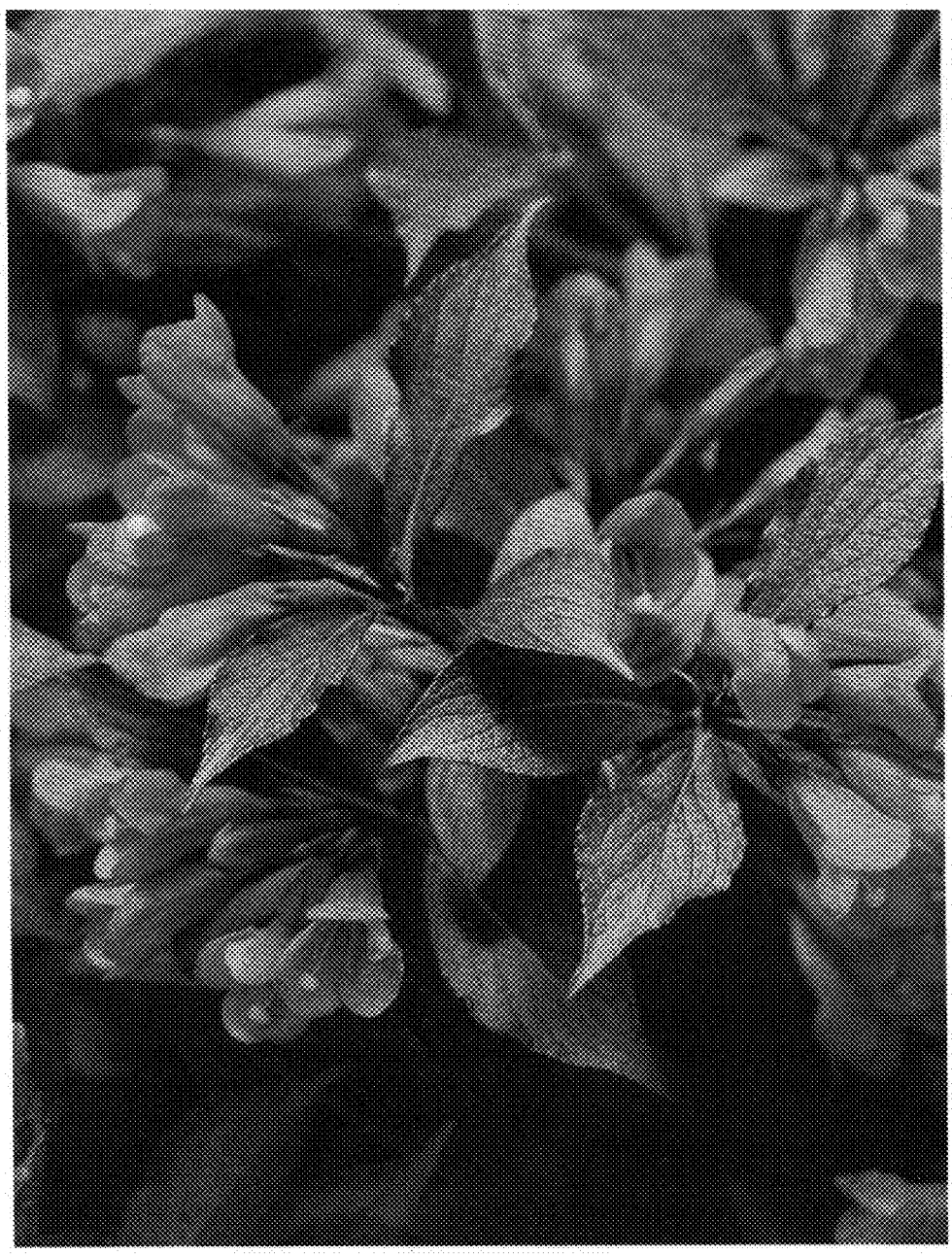

* * * * *